United States Patent [19]
Itoh et al.

[11] Patent Number: 5,886,049
[45] Date of Patent: Mar. 23, 1999

[54] REMEDY FOR AUTOIMMUNE DISEASES

[75] Inventors: Junpei Itoh, Cockeysville, Md.;
Osamu Miyazaki, Kawaguchi, Japan;
Hisao Ekimoto; Michinori Koyama,
both of Tokyo, Japan; Tetsushi Saino,
Yono, Japan; **Lauri Kangas; Anni
Warri**, both of Espoo, Finland;
Christer Granberg, Espoo, Finland

[73] Assignees: Nippon Kayaku Kabushiki Kaisha,
Tokyo, Japan; Orion-yhtyma Oy,
Espoo, Finland

[21] Appl. No.: 844,846

[22] Filed: Apr. 22, 1997

Related U.S. Application Data

[63] Continuation of Ser. No. 448,348, Apr. 25, 1995, abandoned.

[30] Foreign Application Priority Data

Oct. 27, 1992 [JP] Japan ..................................... 4-310772

[51] Int. Cl.⁶ ......................... A61K 31/135; A61K 31/56
[52] U.S. Cl. ............................................ 514/648; 514/171
[58] Field of Search ...................... 514/648, 171

[56] References Cited

U.S. PATENT DOCUMENTS

| | | | |
|---|---|---|---|
| 4,696,949 | 9/1987 | Toivola et al. | 514/648 |
| 5,254,594 | 10/1993 | Niikura et al. | 514/648 |

FOREIGN PATENT DOCUMENTS

| | | | |
|---|---|---|---|
| 0 415 623 | 3/1991 | European Pat. Off. | A61K 31/135 |
| 0415623 | 3/1991 | European Pat. Off. | A61K 31/135 |
| 93/22685 | 11/1993 | WIPO . | |

OTHER PUBLICATIONS

Hosp. Pract., vol. 18, No. 9, 1983, pp. 205–220, XP000646451 W.J. Harrington et al.; "Treateament of idiopathic thrombocytopenic purpura".
Copy of the European Search Report dated Apr. 10, 1997.
British Journal of Dermatology (1989) 121, pp. 135–137; C.J.M. Stephens et al. "Autoimmune progesterone dermatitis responding to Tamoxifen".
Annales De Dermatologie et de Venereologie, vol. 118, No. 8 (1991) pp. 551–555; F. Freychet et al. "La Dermatose Auto–Immune A La Progesterone".
C.J.M. Stephens et al.; "Automimmune progesterone dermatitis responding to Tamaxifn", *British Journal of Dermatology*, vol. 121, No. 1, Jul. 1989, pp. 135–137 (4 pages).
Alan D. Sturgess et al. "Effects of the Oestrogen Antagonist Tamoxifen on Disease Indices in Systemic Lupus Erythematosus", *Journal of Clinical & Laboratory Immunology*, vol. 13, No. 1, Jan. 1984, pp. 11–14 (5 pages).
Madeleine Duvic et al. "Effect of the Anti–Estrogen, Nafoxidine, on NZB/W Autoimmune Disease", *Arthritis and Rheumatism*, vol. 21, No. 4, May 1978, pp. 414–417 (4 pages).
Mech. Manual 17th ED., 1982 pp. 1207–1211.
Stephens et al. Br. Jap. Dent. Vol. 121, (1), pp. 551–555.

*Primary Examiner*—Russell Travers
*Attorney, Agent, or Firm*—Nields, Lemack & Dingman

[57] ABSTRACT

Disclosed is use of nonsteroidal anti-estrogen compounds such as toremifene citrate as active ingredient for treating autoimmune diseases.

6 Claims, 1 Drawing Sheet

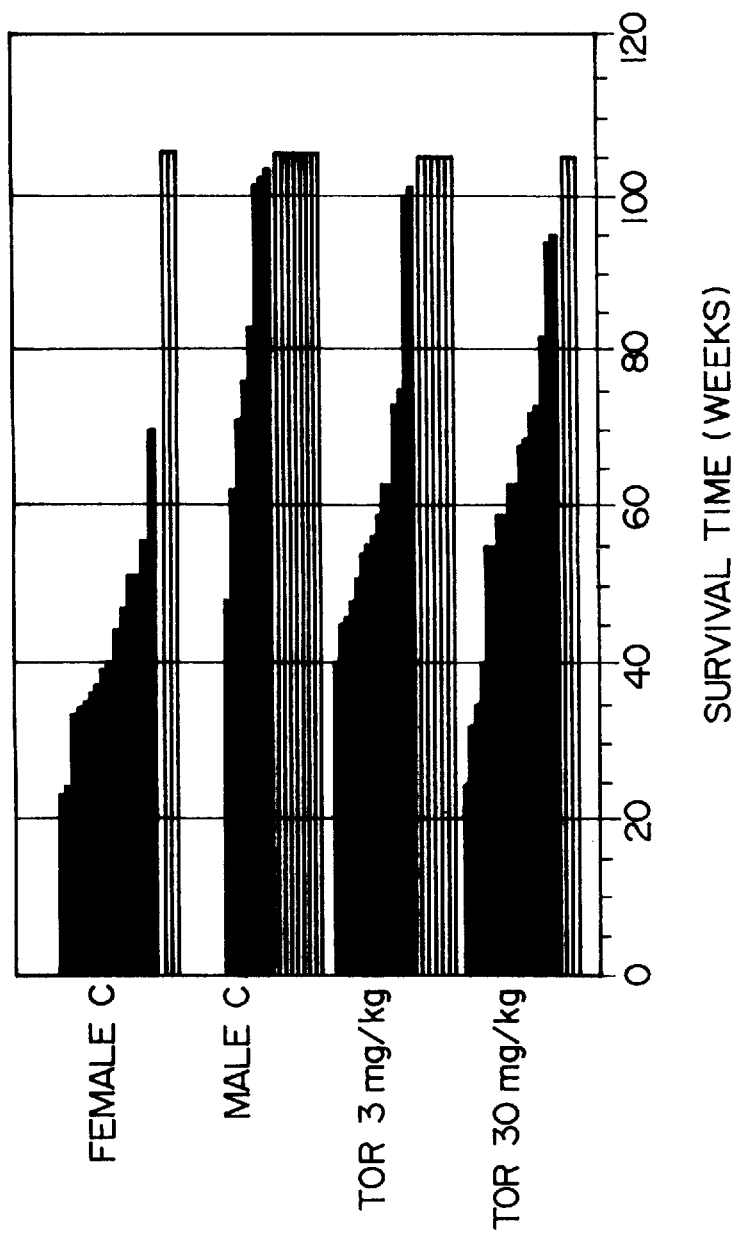
F I G. 1

REMEDY FOR AUTOIMMUNE DISEASES

This application is a continuation of application Ser. No. 08/448,348, now abandoned filed Apr. 25, 1995. Which is a 371 of PCT/JP93/01543 filed Oct. 26, 1993.

TECHNICAL FIELD

The present invention relates to use of nonsteroidal anti-estrogen compounds (hereinafter referred to as nonsteroidal anti-estrogens) such as toremifene, expected as a remedy for autoimmune diseases.

The autoimmune diseases include collagen diseases and the like. In light of affected parts by the diseases, there are mentioned, for example, degenerative diseases of supporting tissues and connective tissues; autoimmune degenerative diseases of salivary glands, particularly Sjögren's disease; autoimmune degenerative diseases of kidneys, particularly systemic lupus erythematodes and glomerulonephritis; autoimmune degenerative diseases of joints, particularly rheumatoid arthritis; and autoimmune degenerative diseases of blood vessels such as generalized necrotizing angitis and granulomatous angitis; and multiple sclerosis.

BACKGROUND ART

Immunosuppressants, nucleic acid antagonists, antimetabolites, etc., are used in the medicinal treatment of autoimmune diseases today. Anti-inflammatory agents, anticoagulants, etc., are also used in the symptomatic therapies of the diseases. The effects of these agents are, however, not yet sufficient.

It is known that the immunosuppressants have side effects of provoking diabetes, renal disorders, infectious diseases, etc. Also the use of the nucleic acid antagonist or antimetabolite is frequently accompanied by side effects such as hepatic disorders and medullary disorders. Thus the medicinal treatment of autoimmune diseases is so far very insufficient.

It has been demanded to develop a remedy for autoimmune diseases which acts on the immune system and which has a function mechanism different from that of conventional drugs for the diseases and less serious side effects.

DISCLOSURE OF INVENTION

After intensive investigations made for the purpose of finding the above-described remedy, the present inventors have found that nonsteroidal anti-estrogens have an excellent therapeutic effect on the autoimmune diseases and thus, based on this finding, completed the present invention.

The present invention relates to a remedy for autoimmune diseases which comprises as active ingredient a nonsteroidal anti-estrogen or a pharmaceutically acceptable salt thereof.

BRIEF DESCRIPTION OF DRAWINGS

FIG. 1 shows survival times of animals (NZB×NZW F1 mice:B/W F1 mice) which accepted different doses of toremifene.

BEST MODE FOR CARRYING OUT THE INVENTION

The nonsteroidal anti-estrogen compounds usable in the present invention are those having a triphenyl $C_2$–$C_5$ alkene or triphenyl $C_2$–$C_5$ alkane skeleton. Preferably, they are $C_2$–$C_5$ alkenes or $C_2$–$C_5$ alkanes having three phenyl substituents at the 1-position and 2-position, wherein any of the phenyl groups may have a substituent such as a mono- or di-lower alkyl ($C_1$–$C_3$) amino lower alkoxy ($C_1$–$C_3$) group, or a hydroxyl group, or the alkyl group in the above alkenes or alkanes may have a substituent such as a halogen.

Examples of these compounds include toremifene (JP-B-4 19973), tamoxifen (JP-B-59 21861), 4-hydroxytamoxifen (JP-A-54 44644), 3-hydroxytamoxifen (JP-A-57 122049) and N-demethyltoremifene or 4-hydroxytoremifene (JP-A-3 163015). Toremifene is particularly preferred. It is well-known that these compounds have an anti-neoplastic effect (see Cancer Chemotherapy and Pharmacology, 17, 109–113 (1986) and the above-mentioned patent publications).

The pharmaceutically acceptable salts thereof include, for example, hydrochlorides, sulfates, citrates, tartrates and phosphates.

Drugs usable in combination with the nonsteroidal anti-estrogens in the medicinal treatment of autoimmune diseases include glucocorticoids (e.g. prednisolone, prednisone, cortisol). Prednisolone is preferred.

The glucocorticoids themselves have an effect of treating the autoimmune diseases. The nonsteroidal anti-estrogens or a pharmaceutically acceptable salt thereof according to the present invention concomitant with the glucocorticoids synergistically improve the effect of treating.

The remedy of the present invention particularly exhibits an excellent remedial effect on systemic lupus erythematodes.

Therefore the present invention relates to the following:

(i) a remedy for autoimmune diseases which comprises as active ingredient a nonsteroidal anti-estrogen or a pharmaceutically acceptable salt thereof;

(ii) a remedy recited in (i), wherein the nonsteroidal anti-estrogen is a compound having a triphenyl $C_2$–$C_5$ alkene or triphenyl $C_2$–$C_5$ alkane skeleton;

(iii) a remedy recited in (i) or (ii), wherein the active ingredient is toremifene or a pharmaceutically acceptable salt thereof;

(iv) a remedy recited in (i) or (ii), wherein the autoimmune diseases are collagen diseases, autoimmune degenerative diseases of kidneys such as nephritis, particularly glomerulonephritis, and autoimmune degenerative diseases of blood vessels, salivary glands and joints;

(v) a remedy recited in (i) or (ii), wherein the autoimmune diseases are systemic lupus erythematodes; and (vi) a remedy recited in (i) or (ii) for concomitant use with a glucocorticoid.

The pharmaceutical composition of the present invention is administered orally, parenterally or intravenously.

Usually, a pharmaceutically effective amount of the active ingredient is used in combination with a suitable medicinal carrier or other auxiliaries. The term "pharmaceutically effective amount" herein means an amount capable of exhibiting the intended pharmacological activity without causing unfavorable side effects. The accurate amount varies in each case depending on various factors such as administration methods, individual natures of the patients and situations in which the patient accepts the remedy and, as a matter of course, structures of derivatives to be administered.

Dose of the active ingredient for adult is usually 10 to 1000 mg/day, preferably 20 to 500 mg/day, more preferably 30 to 300 mg/day.

In the case of the concomitant use, dose of the glucocorticoid for adult is 1 to 100 mg/day, preferably 2 to 60 mg, and that of the nonsteroidal anti-estrogen or the pharmaceutically acceptable salt thereof for adult is 10 to 700 mg/day, preferably 20 to 500 mg/day, more preferably 30 to 300 mg/day.

The medicinal carrier or other auxiliaries generally usable in combination with the active ingredient according to the present invention may be any of solid and liquid ones and usually selected in consideration of an administration route. Examples of the solid carrier include lactose, sucrose, gelatin and agar, and those of the liquid carrier include water, syrup, peanut oil and olive oil. Other suitable carriers and auxiliaries known by those skilled in the art are also usable. The active ingredient according to the present invention can be combined with the carrier or other auxiliaries to form any of various acceptable preparations such as tablets, capsules, suppositories, liquid, emulsion and powder.

In the preparations of the remedy of the present invention, the amount of the nonsteroidal anti-estrogen or the pharmaceutically acceptable salt thereof can widely vary depending on the preparation, etc. Usually, the amount is 0.01~100% by weight, preferably 0.1~70% by weight, and the balance contains the medicinal carrier or other auxiliaries.

MRL/Mp-lpr/lpr mice spontaneously develop a lethal glomerulonephritis, angitis, sialadenitis, polyarthritis, etc., concurrently with the deposition of an immune complex with age. Therefore, they are widely used as experimental models for human systemic lupus erythematodes, Sjögren's disease, rheumatoid arthritis and autoimmune angitis such as multiple arteritis.

The present invention will be explained referring to examples on suppression of lymphadenopathy glomerulonephritis, angitis, sialadenitis and arthritis of MRL/Mp-lpr/lpr mice with the nonsteroidal anti-estrogen compound according to the present invention.

The nonsteroidal anti-estrogen such as toremifene and the pharmaceutically acceptable salt thereof according to the present invention exhibit an excellent remedial effect on degenerative diseases such as autoimmune diseases, for example, systemic lupus erythematodes.

EXAMPLE 1

Treatment of spontaneous autoimmune diseases of MRL/Mp-lpr/lpr mice by administration of 2 [4-(Z)-4-chloro-1,2-diphenyl-1-butenyl]phenoxy-N,N-dimethylethylamine citrate (toremifene citrate)

Eight-week old female MRL/Mp-lpr/lpr mice (Clea Japan, Inc.) were used in this examination. Toremifene citrate (JP-B-4 19973) was suspended in carboxymethylcellulose to prepare a 0.5% suspension. This compound (100 mg/kg) was orally administered to each mouse once a day for 13 weeks.

(A) Inhibition of swelling of spleen and lymph node of MRL/Mp-lpr/lpr mice with toremifene citrate Repeated oral administration of 100 mg/kg of toremifene citrate once a day for 13 weeks inhibited the swelling of the spleen and lymph node of each mouse (see Table 1).

The spleen and lymph nodes of the MRL/Mp-lpr/lpr mice are seriously swollen with age due to the presence of the lymphoproliferation gene (lpr). The lpr codes for the Fas antigen in each mouse. However, in the MRL/Mp-lpr/lpr mice, an abnormality of the genes disturbs the expression of the Fas antigen. As a result, autoreactive T-cells are not subjected to negative selection through the Fas antigen in the thymus and appear in the peripheral tissues to cause the swelling of the lymphoid organs and autoimmune symptoms. The presence of the autoreactive T-cells was confirmed also in the autoimmune diseases of human beings, such as rheumatoid arthritis.

The results of this study indicated that the nonsteroidal anti-estrogen compounds such as toremifene citrate are capable of inhibiting the appearance of the autoreactive T-cells, thereby suppressing the swelling of spleen and lymph node to treat the autoimmune diseases.

TABLE 1

Effect of torermifene citrate 1) on swelling of spleen and lymph node MRL/Mp-1pr/1pr mice

| Group | Number of animals | Spleen weight 4) Body weight | Lymph node 5) weight Body weight |
|---|---|---|---|
| Control 2) | 11 | 2.34 ± 0.74 3) | 6.77 ± 1.70 |
| Toremifene citrate treatment | 12 | 1.38 ± 1.06 | 3.11 ± 1.43 |

1) Toremifene citrate (100 mg/kg) was orally administered to 8-week old mice once a day for 13 weeks.
2) Only 0.5% carboxymethylcellulose was given to the mice of the control group.
3) Standard deviation $$\text{Spleen weight/body weight} = \frac{\text{Weight of spleen}}{\text{Body weight of mouse}} \times 100 \quad 4)$$

$$\text{Lymph node weight/body weight} = \frac{\text{Weight of lymph node}}{\text{Body weight of mouse}} \times 100 \quad 5)$$

(B) Suppression of renal disorder of MRL/Mp-lpr/lpr mouse with toremifene citrate An autopsy was performed on the mice of the control group and the toremifene citrate treated group after the completion of the administration to examine their kidneys pathohistologically. The blood urea nitrogen (BUN) of the serum in each group was examined to confirm changes in the renal function. As shown in Table 2, toremifene citrate ameliorated the glomerulonephritis and healed the renal function in the MRL/Mp-lpr/lpr mice.

The glomerulonephritis of the MRL/Mp-lpr/lpr mice is caused by the deposition of immunocomplexes. Also in the case of the autoimmune diseases such as systemic lupus erythematodes (SLE) of human, the patients suffer from glomerulonephritis concurrent with the deposition of the immunocomplex. The results indicated that the nonsteroidal anti-estrogen compounds such as toremifene citrate are effective remedies for the degenerative diseases of the kidney, such as the SLE with renal syndrome and glomerulonephritis.

TABLE 2

Improvement of renal function and amelioration of glomerulonephritis of MRL/Mp-1pr/1pr mice with toremifene citrate

| Group | Number of animals | Glomerulonephritis 1) | BUN (mg/dl) 2) |
|---|---|---|---|
| Control | 11 | 2.4 ± 0.7 3) | 43.1 ± 23.9 |
| Toremifene citrate treatment | 12 | 1.2 ± 0.7 | 24.6 ± 4.9 |

1 The kidney was fixed in 10% buffered formalin, and then paraffin sections thereof were prepared by an ordinary method to prepare HE and PAS stained specimens. The extent of the disorder of the renal glomeruli was scored and classified into the following groups:

0 (no disorder),
1 (slight disorder),
2 (medium disorder), and
3 (heavy disorder).

Twenty-five renal glomeruli were observed for each mouse and the average thereof was calculated.

2) The BUN was determined with a Fuji Dry Chem Analyzer.

3) Standard deviation.

(C) Inhibition by toremifene citrate of sialadenitis, anqitis and arthritis of MRL/Mp-lpr/lpr mice The salivary gland, renal blood vessel and knee joint of each mouse in the control group and the toremifene citrate treated group were histopathologically examined.

As shown in Table 3, toremifene citrate prevented the mice from being attacked by sialadenitis, angitis and arthritis.

These results indicated that the nonsteroidal anti-estrogen compounds such as toremifene citrate and tamoxifen citrate can be used as the remedy for autoimmune sialadenitis (Sjögren's disease), autoimmune arthritis (chronic articular rheumatism) and autoimmune angitis (necrotizing angitis and granulomatous angitis).

TABLE 3

Effect of toremifene citrate for preventing MRL/Mp-1pr/1pr mice from being attacked by sialadenitis, angitis and arthritis

| Group | Number of animals | Sialadenitis 1) | Angitis 1) | Arthritis 1) |
|---|---|---|---|---|
| Control | 11 | 2.2 ± 0.6 2) | 2.1 ± 0.7 | 1.6 ± 0.9 |
| Toremifene citrate treatment | 12 | 0.9 ± 0.8 | 0.9 ± 0.8 | 0.4 ± 0.5 |

1) The salivary gland, kidney and knee joint were fixed in 10% buffered formalin, and then paraffin sections thereof were prepared by an ordinary method to prepare HE and PAS stained specimens. The extent of the disorder was scored and classified into the following groups:

0 (no disorder),
1 (slight disorder),
2 (medium disorder), and
3 (heavy disorder).

2) Standard deviation.

EXAMPLE 2

Effect of concomitant use of toremifene citrate with glucocorticoid on MRL/MP-lpr/lpr mice Twelve-week old female MRL/Mp-lpr/lpr mice were used in the examination. Thirty miligrams per kg or 15 mg/kg of toremifene citrate (TOR) was orally administered to each mouse twice a day for 9 weeks from the 12th week to the 21st week. A glucocorticoid (prednisolone), 8, 4 and 2 mg/kg/day, were subcutaneously administered to mice once a day as a positive control drug. The concomitant use of tremifene with the glucocorticoid was also carried out according to the same regimen as above. The kidney was taken out from each mouse the day after the completion of the whole administration period and fixed in a PLP fixative. Frozen sections were made from the fixed kidney and used for an immunostaining with an anti-Mac-2 monoclonal antibody (Hybritec Inc., San Diego, USA). The number of Mac-2 positive cells (activated macrophages) invading each of 10 to 20 glomeruli of the kidney, which is hereinafter referred to as Mac 2 number, was counted under a microscopy to determine an average Mac 2 number per glomerulus. The degree of severeness of glomerulonephritis was estimated in terms of the average Mac 2 number (n=13 for each group). Table 4 shows the results.

TABLE 4

Suppression of glomerulonephritis of MRL/Mp-1pr/1pr mice by concomitant use of toremifene citrate with glucocorticoid

| Group | Mac 2 number |
|---|---|
| Control | 7.5 ± 1.5 |
| Toremifene citrate (TOR) | |
| 30 mg/kg | 6.2 ± 1.0 |
| 15 mg/kg | 6.5 ± 1.2 |
| Prednisolone (P) | |
| 8 mg/kg | 5.8 ± 0.8 |
| 4 mg/kg | 7.9 ± 0.7 |
| 2 mg/kg | 9.4 ± 1.0 |
| Control | 11.3 ± 1.2 |
| Prednisolone (P) | |
| 4 mg/kg | 9.1 ± 1.4 |
| 2 mg/kg | 7.7 ± 1.0 |
| P 4 mg/kg & TOR 30 mg/kg (concomitant use) | 4.1 ± 0.5* |
| P 4 mg/kg & TOR 15 mg/kg (concomitant use) | 4.3 ± 0.5* |
| P 4 mg/kg & TOR 7.5 mg/kg (concomitant use) | 3.5 ± 0.5* |
| P 2 mg/kg & TOR 30 mg/kg (concomitant use) | 3.6 ± 0.7* |
| P 2 mg/kg & TOR 15 mg/kg (concomitant use) | 2.8 ± 0.5* |
| P 2 mg/kg & TOR 7.5 mg/kg (concomitant use) | 4.3 ± 0.6* |

*$P < 0.01$ (t-test)

All the groups treated by concomitant use of toremifene citrate (TOR) with prednisolone (P) exhibited significant decrease in Mac 2 number as compared with the control and the prednisolone treated group. On the other hand, the prednisolone treated group and the toremifene citrate treated group did not exhibit any significant decrease in Mac 2 number as compared with the control. The results of these tests indicates that the concomitant use of the both drugs synergistically suppresses the glomerulonephritis.

EXAMPLE 3

Comparison of survival time

NZB×NZW mice (B/W F1 mice) were used as a pathological model of autoimmune diseases (systemic lupus erythematodes). Effect of toremifene citrate on the survival time of the animals was investigated.

Experimental animals:

F1-hybrids of NZB (female) and NZW (male) mice (B/W F1 mice): Imported from Bomholtgaard, Denmark at the age of five weeks.

Test groups and doses:

Control (male): administration polyethyleneglycol (peg) 3 times a week per os

Control (female): administration peg 3 times a week per os

Toremifene citrate 30 mg/kg/day: administration 70 mg/kg in polyethylene glycol solution 3 times a week per os to female NZB×NZW F1 mice Toremifene citrate 3 mg/kg/day: administration 7 mg/kg in polyethylene glycol solution 3 times a week per os to female NZB×NZW F1 mice The survival time of the animals in different test groups is presented in FIG. 1. All but two female control animals have died during the almost two years' follow-up time. Fifty percents of the animals in this group died before/at the age of 40 weeks, and 20% (4/20) were alive after one year.

In the male control group, five animals died during the first 24 weeks (not shown in FIG. 1) due to aggressive behaviour and thereby acquired infection. These five were excluded from the results. Forty-seven percents of the male control mice are still alive after almost two years' time.

In both toremifene treatment groups the life span of the animals has lengthened clearly when compared to the female control animals. In the 3 mg/kg toremifene treatment group only one (1/20) animal had died at/before the age of 40 weeks and three (3/20) animals in the 30 mg/kg toremifene group.

After one year 80% and 85% of the animals were alive in the 3 mg/kg and 30 mg/kg toremifene treated groups, respectively, which is nearer the percentage of the male control animals (≈90%) than that of the female control group (20%).

Moreover, 25% (5/20) and 10% (2/20) of the animals are still alive after almost two years' time in the lower and higher toremifene dosage group, respectively.

The follow-up data of 60 female and 15 male F1-hybrids of NZB×NZW F1 mice (B/W F1 mice) show that toremifene treatment has clearly extended the life span of female mice.

EXAMPLE 4

Examples of preparations comprising the nonsteroidal anti-estrogen or the pharmacologically acceptable salt thereof as active ingredient will be given below, which by no means limit the preparations of the present invention.

PREPARATION EXAMPLE 1

Formulation of prepared 200 mg tablet.

| | |
|---|---|
| Toremifene citrate | 20 mg |
| Starch | 85 mg |
| Lactose | 90 mg |
| Magnesium stearate | 5 mg |

PREPARATION EXAMPLE 2

Formulation of prepared 200 mg tablet.

| | |
|---|---|
| Tamoxifen citrate | 20 mg |
| Starch | 85 mg |
| Lactose | 90 mg |
| Magnesium stearate | 5 mg |

We claim:

1. A method for treating systemic lupus eryematodes comprising administering to a patient suffering from systemic lupus erythematodes a therapeutically effective amount of toremifene or a pharmaceutically acceptable salt thereof.

2. A method according to claim 1, wherein toremifene is administered together with a glucocorticoid.

3. A product comprising toremifene or a pharmaceutically acceptable salt thereof and a glucocorticoid as a combined preparation for treating autoimmune diseases.

4. The method according to claim 2, wherein said glucocorticoid is prednisolone.

5. The product of claim 3, wherein said glucocorticoid is prednisolone.

6. A method for treating autoimmune diseases comprising administering to a patient suffering from an autoimmune disease a therapeutically effective amount of tore mifene or a pharmaceutically acceptable salt thereof together with a glucocorticoid.

* * * * *